(12) United States Patent
Marshall et al.

(10) Patent No.: US 10,058,695 B2
(45) Date of Patent: Aug. 28, 2018

(54) COLLAPSIBLE EXTRAVASCULAR LEAD

(71) Applicant: Medtronic, Inc., Minneapolis, MN (US)

(72) Inventors: Mark T. Marshall, Forest Lake, MN (US); Vladimir P. Nikolski, Blaine, MN (US); Nathan L. Olson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/973,818

(22) Filed: Dec. 18, 2015

(65) Prior Publication Data

US 2016/0175580 A1    Jun. 23, 2016

Related U.S. Application Data

(60) Provisional application No. 62/093,633, filed on Dec. 18, 2014.

(51) Int. Cl.
*A61N 1/05*    (2006.01)

(52) U.S. Cl.
CPC ............ *A61N 1/05* (2013.01); *A61N 1/0504* (2013.01); *A61N 1/0563* (2013.01)

(58) Field of Classification Search
None
See application file for complete search history.

(56) References Cited

U.S. PATENT DOCUMENTS

| | | | |
|---|---|---|---|
| 4,154,247 A | 5/1979 | O'Neill | |
| 4,998,975 A | 3/1991 | Cohen et al. | |
| 5,105,826 A | 4/1992 | Smits et al. | |
| 5,388,578 A | 2/1995 | Yomtov et al. | |
| 5,531,779 A | 7/1996 | Dahl et al. | |
| 5,772,590 A | 6/1998 | Webster, Jr. | |
| 5,855,592 A * | 1/1999 | McGee | A61N 1/3918 600/374 |
| 7,047,086 B2 | 5/2006 | Taskiran et al. | |
| 7,349,742 B2 | 3/2008 | Heil et al. | |
| 7,890,191 B2 | 2/2011 | Rutten et al. | |
| 7,899,555 B2 | 3/2011 | Morgan et al. | |
| 8,050,773 B2 | 11/2011 | Zhu | |
| 2010/0082086 A1* | 4/2010 | Zhu | A61N 1/0558 607/117 |

(Continued)

FOREIGN PATENT DOCUMENTS

EP    1323451 A2    7/2003

OTHER PUBLICATIONS (PCT/US2015/066628) PCT Notification of Transmittal of the International Search Report and the Written Opinion of the International Searching Authority, dated Mar. 9, 2016, 9 pages.

*Primary Examiner* — Ankit D Tejani

(57) ABSTRACT

An implantable medical electrical lead having an elongate lead body having a proximal end and a distal portion. A plurality of defibrillation electrodes coupled to the distal portion is included, the plurality of electrodes being transitionable from a first configuration in which the defibrillation electrodes are biased in an expanded configuration to a second configuration in which the defibrillation electrodes are in a collapsed configuration. A joint slideably disposed around a portion of the lead body is included, at least a portion of the plurality of defibrillation electrodes being coupled to the joint.

27 Claims, 6 Drawing Sheets

(56) References Cited

U.S. PATENT DOCUMENTS

| | | | |
|---|---|---|---|
| 2013/0006332 A1* | 1/2013 | Sommer | A61N 1/056 607/62 |
| 2014/0324043 A1 | 10/2014 | Terwey et al. | |
| 2014/0330208 A1 | 11/2014 | Christie et al. | |
| 2014/0330287 A1 | 11/2014 | Thompson-Nauman et al. | |
| 2014/0330325 A1 | 11/2014 | Thompson-Nauman et al. | |
| 2014/0330326 A1 | 11/2014 | Thompson-Nauman et al. | |
| 2014/0330327 A1 | 11/2014 | Thompson-Nauman et al. | |
| 2014/0330328 A1 | 11/2014 | Christie et al. | |
| 2014/0330329 A1 | 11/2014 | Thompson-Nauman et al. | |
| 2015/0306375 A1 | 10/2015 | Marshall et al. | |
| 2015/0306410 A1 | 10/2015 | Marshall et al. | |

\* cited by examiner

COLLAPSIBLE EXTRAVASCULAR LEAD

CROSS-REFERENCE TO RELATED APPLICATION

This application is related to and claims priority to U.S. Provisional Patent Application Ser. No. 62/093,633, filed Dec. 18, 2014, entitled COLLAPSIBLE SUBSTERNAL LEAD, the entirety of which is incorporated herein by reference.

TECHNICAL FIELD

The present application relates to electrical stimulation leads and, more particularly, electrical stimulation leads with improved defibrillation, sensing, and/or pacing capabilities for use in extravascular applications, including but not limited to subcutaneous or substernal applications.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of ventricular fibrillation, the use of an implantable cardioverter defibrillator (ICD) system has been shown to be beneficial at preventing SCD. An ICD system includes an ICD that is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Electrical leads being utilized in subcutaneous systems typically include linear arrays of electrodes positioned on the lead body. Thus, the delivery of electrical stimulation therapy to the heart with current lead designs provides limited therapy vectors depending on the shape of the lead body, for which the electrical energy may impact the heart. That is, linear lead designs provide narrow vectors of treatment. However, because the size and position of the heart within a patient is variable, it is desirable to provide a wider array of therapy vectors to provide defibrillation shocks, pacing pulses, and the ability to sense a cardiac depolarization across a wider area of the heart.

SUMMARY

The present application advantageously provides an implantable medical electrical lead having an elongate lead body having a proximal end and a distal portion. A plurality of defibrillation electrodes coupled to the distal portion is included, the plurality of electrodes being transitionable from a first configuration in which the defibrillation electrodes are biased in an expanded configuration to a second configuration in which the defibrillation electrodes are in a collapsed configuration. A joint slideably disposed around a portion of the lead body is included, at least a portion of the plurality of defibrillation electrodes being coupled to the joint.

In another embodiment, the implantable medical electrical lead has an elongate lead body having a proximal end and a distal portion. A plurality of defibrillation electrodes coupled to the distal portion are included, the plurality of electrodes defining respective proximal and distal ends, the plurality of defibrillation electrodes being transitionable from a first configuration in which the defibrillation electrodes are biased in an expanded configuration in which the plurality of electrodes extend radially outward from the lead body to a second configuration in which the defibrillation electrodes are in a collapsed configuration in which the plurality of electrodes are substantially parallel to the lead body. A joint slideably disposed around a portion of the lead body is included, the distal ends of the plurality of the defibrillation electrodes being disposed within a portion of the joint.

In yet another embodiment, the implantable medical electrical lead has an elongate lead body having a proximal end and a distal portion. A plurality of defibrillation electrodes coupled to the distal portion are included, the plurality of electrodes defining respective proximal and distal ends, the plurality of defibrillation electrodes being transitionable from a first configuration in which the defibrillation electrodes are biased in an expanded configuration in which the plurality of electrodes extend radially outward from the lead body to a second configuration in which the defibrillation electrodes are in a collapsed configuration in which the plurality of electrodes are substantially parallel to the lead body. A joint slideably disposed around a portion of the lead body is included, the distal ends of the plurality of the defibrillation electrodes being disposed within a portion of the joint. A shaft disposed between the proximal and distal ends of the plurality of defibrillation electrodes is included, the shaft defining a first side and a second side opposite the first side, the shaft including a plurality of longitudinally spaced and recessed electrodes on the first side and at least one of the plurality of defibrillation electrodes on the second side. The joint abuts the proximal end of the shaft when the plurality of defibrillation electrodes are disposed in the first configuration.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1:
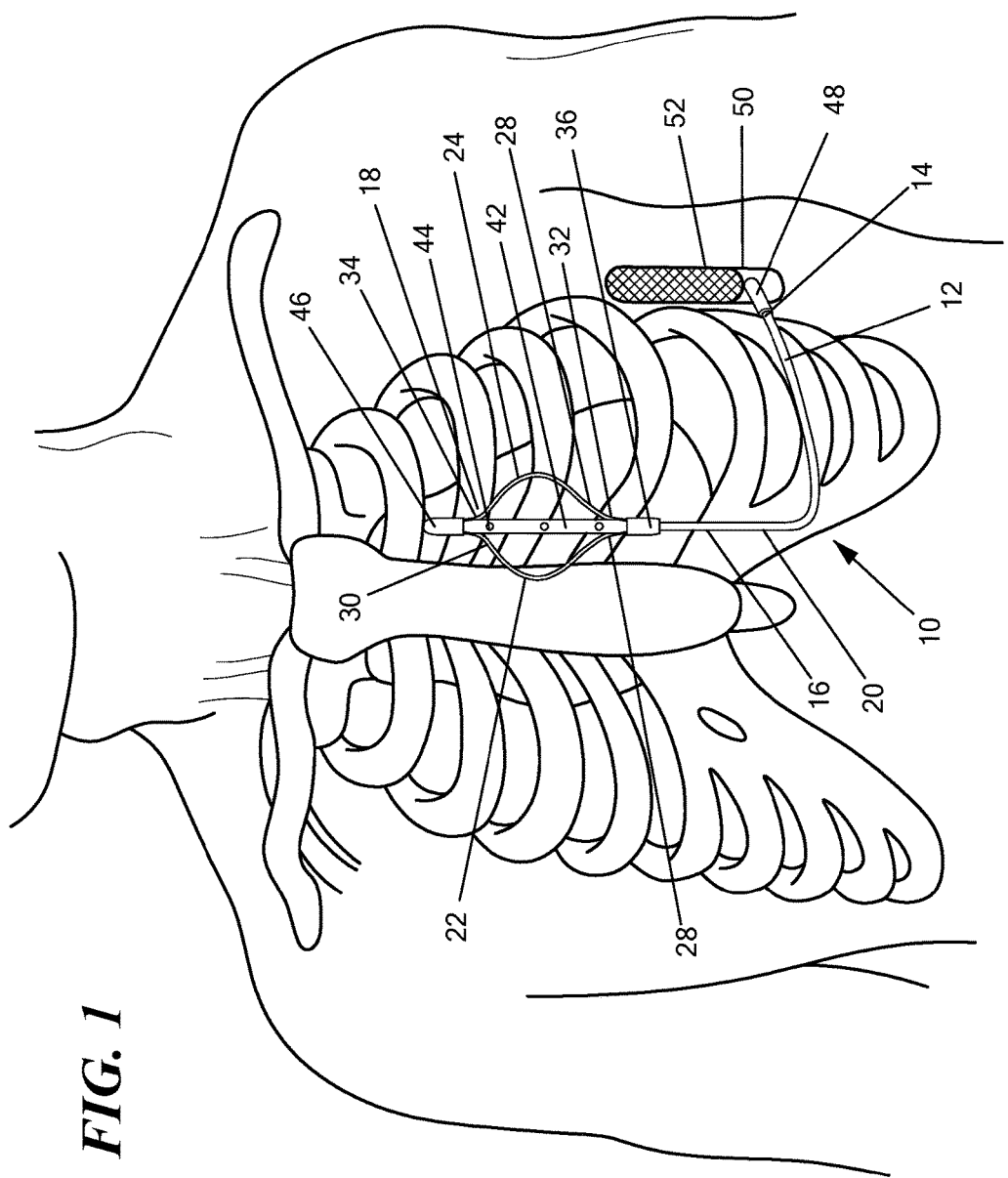
FIG. 1 is a front view of an exemplary medical electrical lead and device implanted within the patient and constructed in accordance with the principles of the present application.
Figure 2:
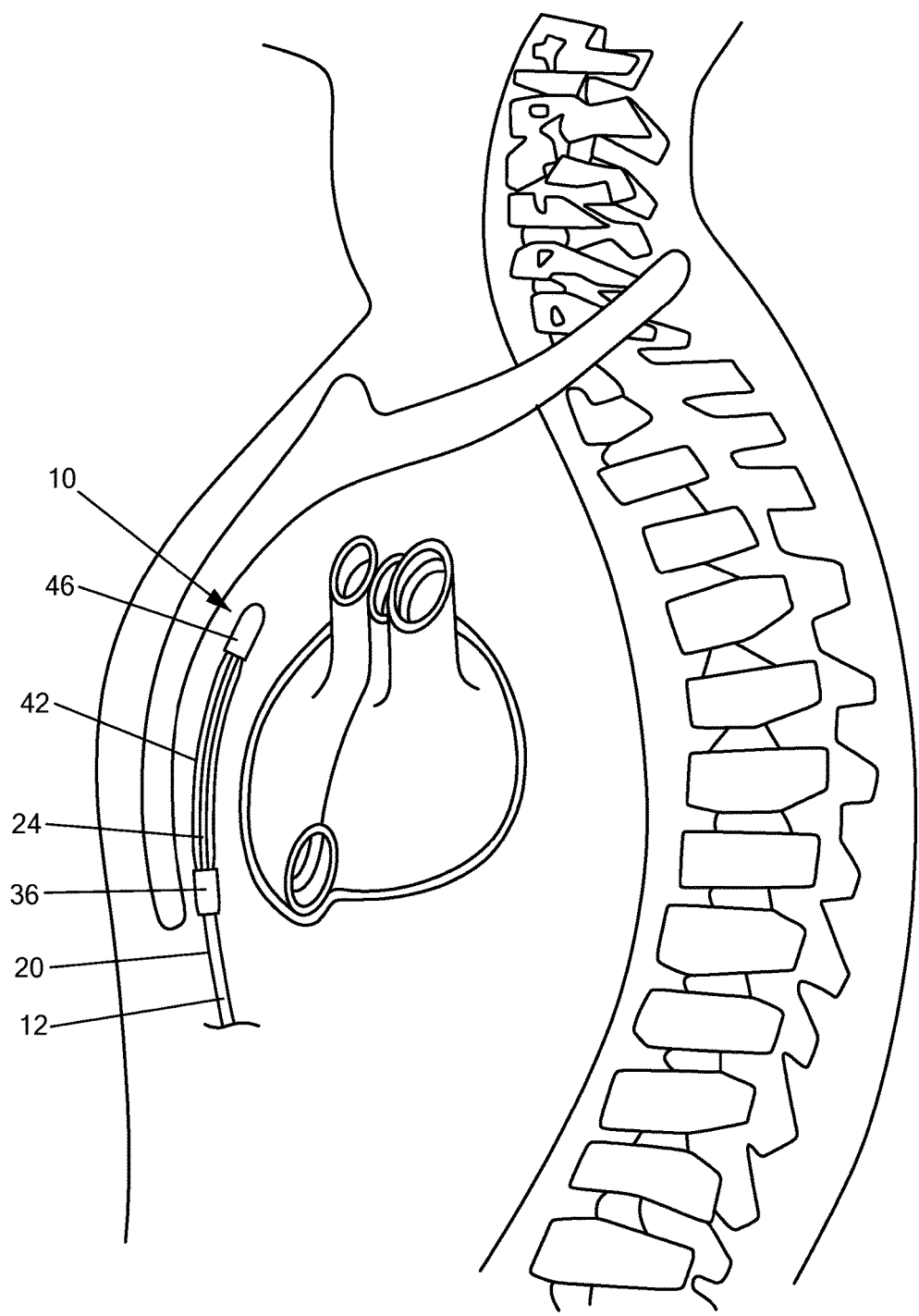
FIG. 2 is a side of the medical electrical lead shown in FIG. 1 showing the lead implanted underneath the sternum.
Figure 3:
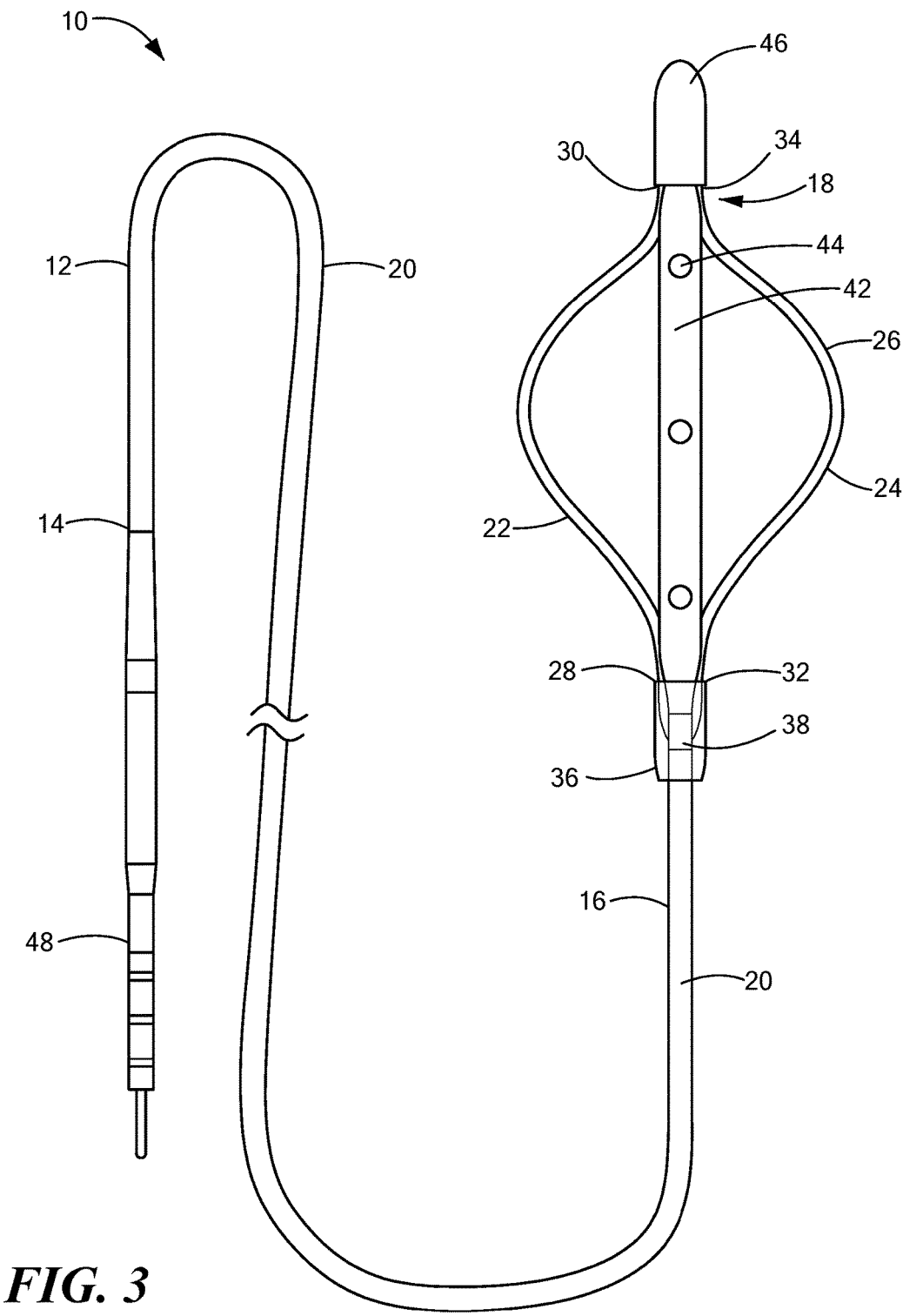
FIG. 3 is a front view of the exemplary medical electrical lead shown in FIG. 1.

Referring now to the drawings in which like reference designators refer to like elements, there is shown in FIGS. 1-3 an exemplary medical electrical lead constructed in accordance with the principles of the present application and designated generally as "10." The lead 10 may include an elongated lead body 12 sized to be implanted extra-throacically (e.g., subcutaneously or submuscularly as illustrated in (FIG. 1) or intra-thoracically (e.g., substernally as illustrated in FIG. 2) proximate the heart. For example, the lead 10 may extend subcutaneously toward the center of the torso of a patient, for example, toward the xiphoid process of the patient. At a position proximate the xiphoid process, the lead body 12 may bend or otherwise turn and extend superiorly, either extra-thoracically (e.g., subcutaneously or submuscularly) above the sternum and/or ribcage, or intra-thoracically (e.g., substernally) underneath the sternum and/or ribcage, in a direction substantially parallel to the sternum. Although illustrated in FIG. 1 as being offset laterally from and extending substantially parallel to the sternum, the lead 10 may be implanted at other locations, such as over the sternum, under the sternum (FIG. 2), offset to the right of the sternum, angled lateral from the proximal or distal end of the sternum, or the like.

In one example, the distal portion of lead 10 may be implanted in a substernal location. The substernal location may be within the anterior mediastinum. The anterior mediastinum may be viewed as being bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein. In one example, the distal portion of lead 10 may be implanted substantially within the loose connective tissue and/or substernal musculature of the anterior mediastinum, e.g., extending superior along the posterior side of the sternum.

In other embodiments, the distal portion of lead 10 may be implanted in other non-vascular, extra-pericardial locations, including the gap, tissue, or other anatomical features around the perimeter of and adjacent to, but not attached to, the pericardium or other portion of the heart and not above the sternum or ribcage. As such, lead 10 may be implanted anywhere within the "substernal space" defined by the undersurface between the sternum and/or ribcage and the body cavity but not including the pericardium or other portion of the heart. The substernal space may alternatively be referred to by the terms "retrosternal space" or "mediastinum" or "infrasternal" as is known to those skilled in the art and includes the anterior mediastinum. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62. In other words, the distal portion of lead 10 may be implanted in the region around the outer surface of the heart, but not attached to the heart.

The lead body 12 may have a generally tubular or cylindrical shape and may define a diameter of approximately 3-9 French (Fr), however, lead bodies 12 of less than 3 Fr and more than 9 Fr may also be utilized. In another configuration, the lead body 12 may have a flat, ribbon, or paddle shape along at least a portion of the length of the lead body 12. In such an example, the width across the lead body 12 may be between 1-3.5 mm. Other lead body 12 designs may be used without departing from the scope of this application. The lead body 12 of lead 10 may be formed from a non-conductive material, including silicone, polyurethane, fluoropolymers, mixtures thereof, and other appropriate materials, and shaped to form one or more lumens (not shown), however, the techniques are not limited to such constructions. The lead body 12 may be fabricated to be biased in a desired configuration, or alternatively, may be manipulated by the user into the desired configuration. For example, the lead body 12 may be composed of a malleable material such that the user can manipulate the distal portion into a desired configuration where it remains until manipulated to a different configuration.

The lead body 12 may include a proximal end 14 and a distal portion 16 connected to an electrical stimulation therapy portion 18, the electrical stimulation therapy portion 18 configured to deliver electrical energy to the heart and/or sense electrical energy (or signals) of the heart. In some instances the electrical stimulation therapy portion 18 may be anchored to a desired position within the patient, for example, substernally or subcutaneously by, for example, suturing the electrical stimulation therapy portion 18 to the patient's musculature, tissue, or bone at the xiphoid process entry site. Alternatively, the electrical stimulation therapy portion 18 may be anchored to the patient or through the use of rigid tines, prongs, barbs, clips, screws, and/or other projecting elements or flanges, disks, pliant tines, flaps, porous structures such as a mesh-like element that facilitate tissue growth for engagement, bio-adhesive surfaces, and/or any other non-piercing elements. The anchoring feature(s) may be located near a distal end of the lead body 12, near the portion of lead body 12 that bends or curves near the xiphoid process, in both of these locations, or in one or more other locations. The lead body 12 may further define a substantially linear portion 20 as it curves around the xiphoid process and extends superiorly toward the heart. In other instances, lead body 12 may not include any anchoring features. Instead, the deployed configuration of lead 10 may serve as the mechanism by which lead body 12 is anchored.

As shown in FIG. 1, the electrical stimulation therapy portion 18 may include a first defibrillation electrode 22 and a second defibrillation electrode 24 extending radially outward from the lead body 12. The defibrillation electrodes 22 and 24 may be elongate coil electrodes formed by a coiled conductor. The conductor may be formed of one or more conductive polymers, ceramics, metal-polymer composites, semiconductors, metals or metal alloys, including but not limited to, one of or a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole and other polymers. In another configuration, the defibrillation electrodes 22 and 24 may be a flat ribbon electrode, a paddle electrode, a braided or woven electrode, a mesh electrode, a directional electrode, a patch electrode or another type of electrode configured to deliver a defibrillation shock to the patient's heart.

The defibrillation electrodes 22 and 24 may be flexible and biased in an expanded configuration 26 in which each of the defibrillation electrodes 22 and 24 define an arcuate configuration extending radially outward from lead body 12. Although the defibrillation electrodes 22 and 24 are shown as symmetric arcs, it is contemplated that the expanded configuration 26 of the defibrillation electrodes 22 and 24 may form any shape, for example, undulations, and may be symmetric or asymmetric with respect to each other. For example, defibrillation electrode 22 may form an undulation pattern whereas defibrillation electrode 24 may form an arcuate pattern. The defibrillation electrodes 22 and 24 may be connected to a common conductor such that a voltage may be applied to each of the defibrillation electrodes 22 and 24 simultaneously for delivery of defibrillation shocks to the heart. Alternatively, each of the defibrillation electrodes 22 and 24 may be connected to separate conductors such that each of the defibrillation electrodes 22 and 24 may be charged with a different or the same polarity to provide for a variety of defibrillation shock vectors to the heart.

Continuing to refer to FIGS. 1-3, in an exemplary configuration, the defibrillation electrodes 22 and 24 are substantially planar when in the first expanded configuration 26 such that when disposed subcutaneously or substernally the defibrillation electrodes 22 and 24 lay flat against the tissue. That is, the defibrillation electrodes 22 and 24 may lay substantially in the same plane when the defibrillation electrodes 22 and 24 are disposed in the expanded configuration 26. In other configurations, the defibrillation electrodes 22 and 24 may be disposed at an oblique angle with respect to the lead body 12 and each of the defibrillation electrodes 22 and 24 may be disposed at different oblique angles. Although the defibrillation electrodes 22 and 24 are each shown as one continuous coil electrode, it is further contemplated that each of the defibrillation electrodes 22 and 24 may include multiple electrically connected segments that are electrically insulated from each other. For example, each of the defibrillation electrodes 22 and 24 may be disposed along a conductor with an electrically insulating material, for example, polyurethane, disposed between each segment such that a particular defibrillation shock vector may be created from each of segments of the defibrillation electrodes 22 and 24. In another configuration, the electrodes 22 and 24 may be completely or partially coated with an electrically insulating material, for example, tantalum pentoxide, which prevents the transmission of low voltage electrical pulses, such as pacing pulses, but allows the transmission of high voltage defibrillation shocks.

Continuing to refer to FIGS. 1-3, the first defibrillation electrode 22 includes a proximal end 28 and a distal end 30. Similarly, the second defibrillation electrode 24 includes a proximal end 32 and a distal end 34. The proximal ends 28 and 32 may define a slideable joint 36 with a portion of the lead body 12. In particular, the proximal ends 28 and 32 may be fixedly connected on opposite sides to a cap, box, or junction slideably and circumferentially disposed around a portion of the lead body 12. The proximal ends 28 and 32 may be affixed to an inner portion of the joint 36 by methods known in the art, for example, welding.

In an alternative configuration, the lead body 12 may define an electrically conductive outer surface 38 (shown in FIG. 3) at the location of the joint 36. For example, a conductor such as platinum, on a portion of the distal portion 16 configured to transfer electricity from within the lead body 12 to the proximal ends 28 and 32 when the defibrillation electrodes 22 and 24 are in the expanded confirmation 26. The position of the electrically conductive outer surface 38 on the lead body 12 may correspond to the position of the proximal ends 28 and 32 when the defibrillation electrodes 22 and 24 are in the expanded configuration 26 to provide a voltage to the defibrillation electrodes 22 and 24 when the distal ends 28 and 32 come into contact with the electrically conductive outer surface.

Figure 4:
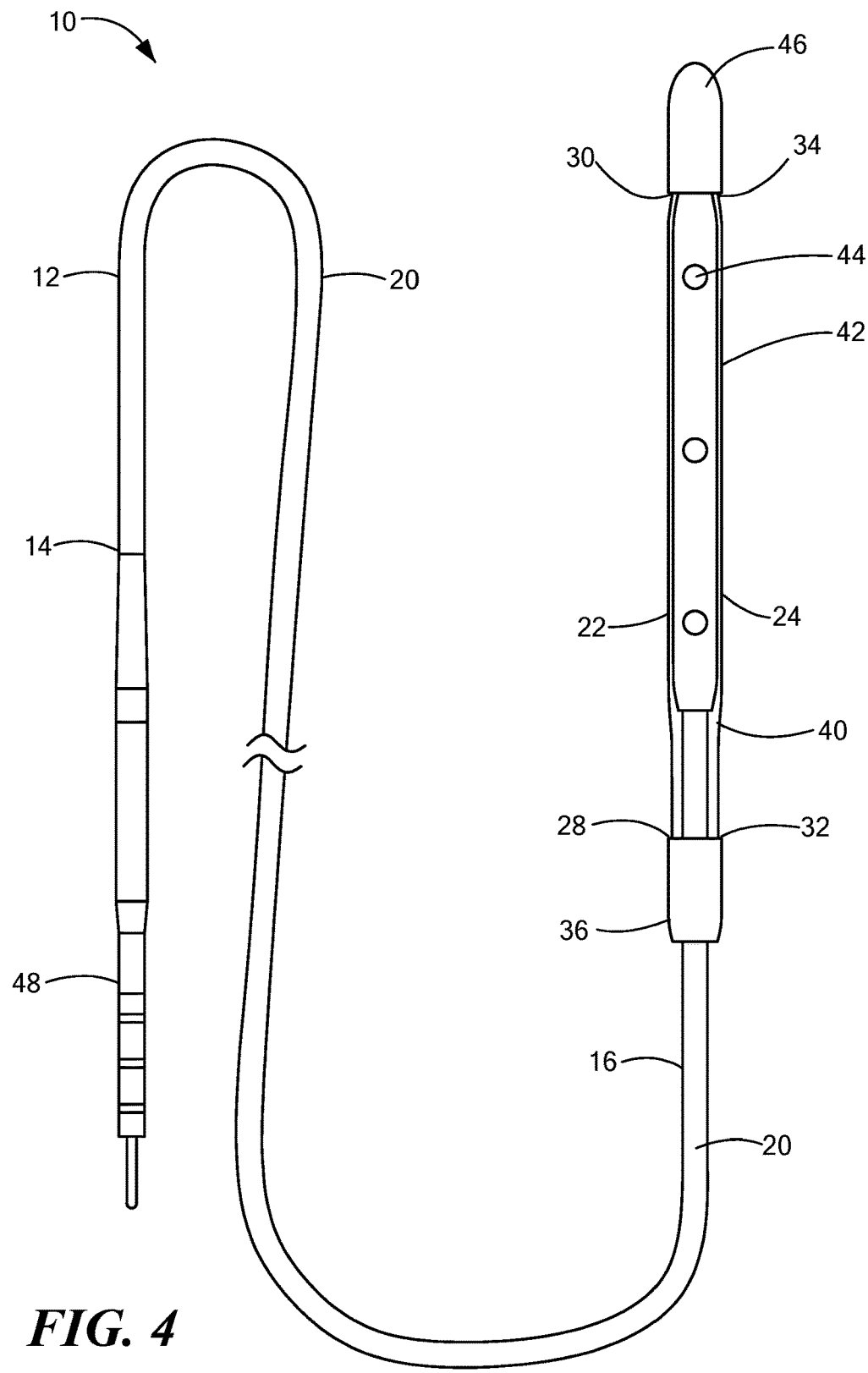
FIG. 4 is a front view of the exemplary medical electrical lead shown in FIG. 1 in a collapsed configuration.

The joint 36 may be biased in the position shown in FIGS. 1-3 and may move from a first position in which the defibrillation electrodes 22 and 24 are in the expanded configuration 26 to a second position proximal to the first position in which the defibrillation electrodes 22 and 24 are in a collapsed configuration 40 (seen in FIG. 4). The defibrillation electrodes 22 and 24 push on the joint 36 when the defibrillation electrodes 22 and 24 are collapsed by an external force. For example, the lead body 12 including the distal portion 16 may be implanted substernally or subcutaneously through a sheath and/or and introducer device such as a tunneling tool defining a lumen or channel therein. The elongate body 12 and the electrical stimulation therapy portion 18 may be slideably received within the sheath or tunneling tool for substernal or subcutaneous implantation. When disposed within the tunneling tool or sheath, the defibrillation electrodes 22 and 24 may be pushed by the walls of the tunneling tool or sheath such that the defibrillation electrodes 22 and 24 push on the joint 36 to collapse the defibrillation electrodes 22 and 24 into the second position, e.g., the collapsed configuration 40. The defibrillation electrodes 22 and 24 may define a substantially linear configuration when in the collapsed configuration 40 such that the defibrillation electrodes 22 and 24 are substantially parallel with the major longitudinal axis of the lead body 12.

Continuing to refer to FIGS. 1-3, abutting the joint 36 when the defibrillation electrodes 22 and 24 are in the expanded configuration may be a shaft 42 extending from the proximal ends to the distal ends of the defibrillation electrodes 22 and 24. The shaft may be substantially flat or cylindrical in shape and may define a smaller or wider width or diameter to that of lead body 12. In the expanded configuration, the defibrillation electrodes 22 and 24 and the shaft 42 may be substantially planar to each other. In one configuration, the proximal end of the shaft 42 is sized to be fitted within the distal end of the joint such that the joint stops sliding by mechanical interference from the proximal end of the shaft 42. In another configuration, the joint 36 and the shaft 42 may releasably engage by, for example, snap fit or bayoneting connection when the defibrillation electrodes 22 and 24 transition from the collapsed configuration to the expanded configuration. The shaft 42 may include electrically insulating materials similar to that of the lead body 12 and may be in electrical communication with one or more conductors within the lead body 12. In an exemplary configuration, the shaft 42 is rigid and substantially linear in configuration although in other configurations the shaft 42 may be malleable to flexible and may take a non-linear shape.

Raised, recessed, or flush with a portion of the shaft may be a plurality of electrodes 44 in electrical communication with a conductor within the lead body 12. The plurality of electrodes 44 may be longitudinally spaced along the major longitudinal axis of the shaft 42. In the example illustrated in FIGS. 1-3, for example, three electrodes 44 are located along the major longitudinal axis of the shaft 42. However, lead 10 may have fewer electrodes 44 (including only a single electrode) or more than three electrodes 44. In one configuration, the electrodes 44 are directional electrodes, e.g., circular-shaped directional electrodes in the illustrated example. However, in other configurations, the electrodes 44 may be any of a number of different types of electrodes, including ring electrodes, short coil electrodes, paddle electrodes, hemispherical electrodes, directional electrodes of other shapes, or the like. Electrodes 44, additionally or alternatively, may be radially disposed about the shaft 42.

Electrodes 44 may be disposed to provide electrical stimulating therapy toward a particular direction.

In an exemplary configuration, the distal end of the lead body 12 is connected to the proximal end of the shaft 42. In one configuration, the distal end of the lead body 12 extends through the joint 36 and passed the proximal ends 28 and 32 of the defibrillation electrodes 22 and 24. In another configuration, the lead body 12 and the shaft 42 are engaged within the joint 36. In yet another configuration, the shaft 42 may circumferentially surround the lead body 12 between the proximal and distal ends of the defibrillation electrodes 22 and 24. In such a configuration, the plurality of electrodes 44 may be recessed within the shaft 42 and disposed along the lead body 12 within the shaft 42.

The plurality of electrodes 44 may be electrically insulated from each other and may be configured to deliver pacing pulses to and/or sense cardiac depolarizations from the heart. The plurality of electrodes 44 are coupled to one or more separate conductors than the conductor(s) coupled to the defibrillation electrodes 22 and 24. In such a configuration, current may flow between one or both of the defibrillation electrodes 22 and 24 and one or more of the plurality of electrodes to create different electrical stimulation therapy vectors for treatment of the heart. Additionally, current may flow between one or both defibrillation electrodes 22 and 24 and the housing electrode. Current may also flow from one or more of electrodes 44 to the housing electrode. In other configurations, the plurality of electrodes 44 may be short coil electrodes that for segments of another defibrillation electrode, for example, a third defibrillation electrode. The third defibrillation electrode may be similar to or different from defibrillation electrodes 22 and 24 and be configured to deliver a defibrillation shocks to the patient's heart. In this case, at least a portion of the short coil electrodes may serve the dual high voltage therapy and low voltage therapy (or sensing) functions.

The defibrillation electrodes 22 and 24 may, in one example, have a length of between approximately 5-10 cm. Likewise, shaft 42 may have a length between 5-10 cm in one example. However, the defibrillation electrodes 22 and 24 and shaft 42 may have lengths less than 5 cm and greater than 10 cm in other embodiments.

Disposed at the distal end of the distal portion may be a tip 46. The distal ends 30 and 34 may be retained within the tip 46 which may be fixed at the distal end of the lead body 12. The tip 46 may further be in electrical communication with a conductor extending from the lead body 12 and through the shaft 42. The tip 46 may be conductive and may be configured to function as a low voltage electrode, similar to electrodes 44, to deliver electrical stimulation therapy to and/or sense cardiac electrical signals from the heart. In this case, tip 46 is electrically isolated from defibrillation electrodes 22 and 24 to function as an electrode separate from any of electrodes 22, 24, and 44. Alternatively, the tip 46 may be non-conductive and serve as a distal joint to mechanically couple the defibrillation electrodes 22, 24, and shaft 42. In yet another configuration, the tip 46 may be configured to provide electricity to distal ends 30 and 34 of the defibrillation electrodes 22 and 24.

Figure 5:
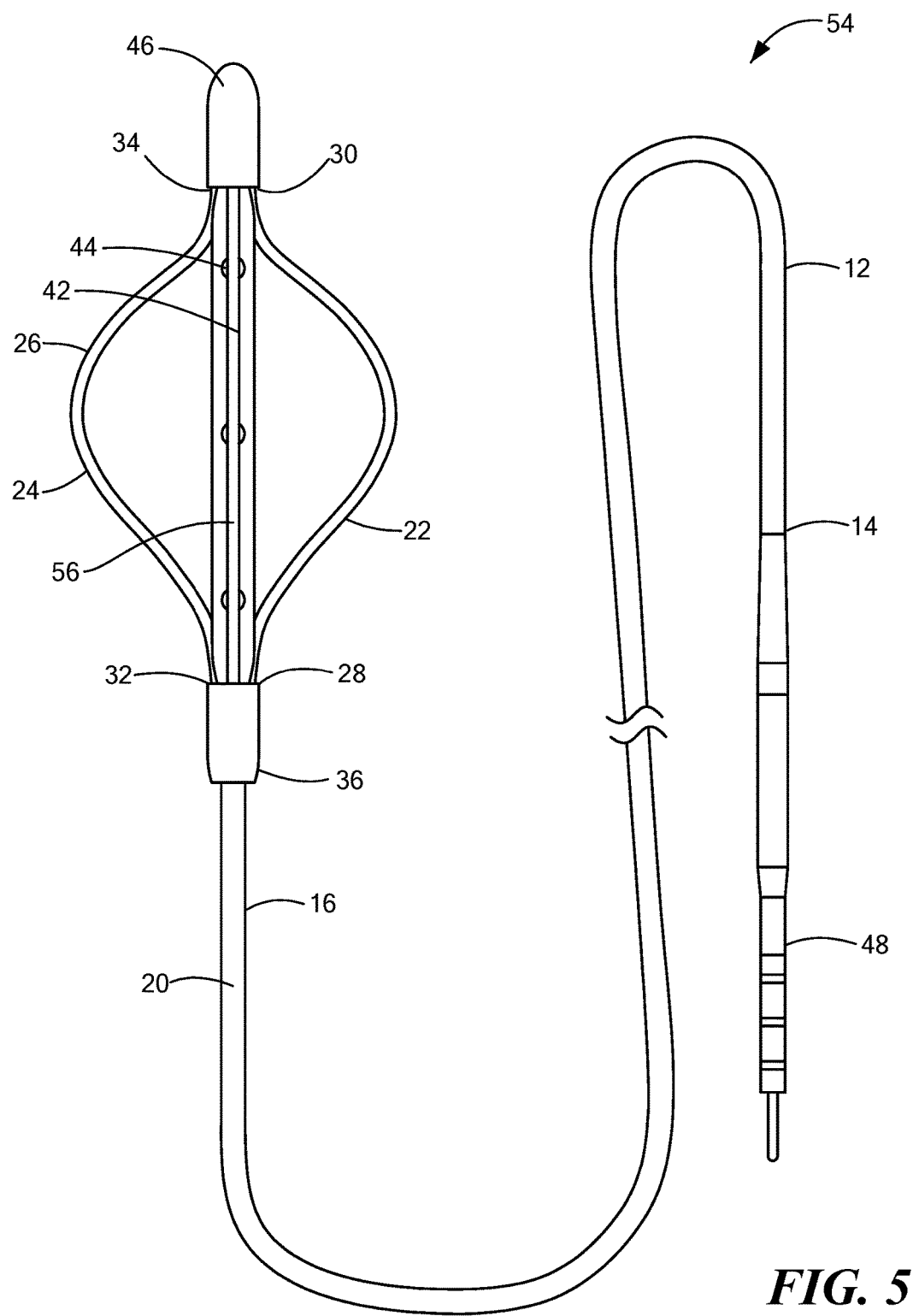
FIG. 5 is a back view of another medical electrical lead constructed in accordance with the principles of the present application.

Continuing to refer to FIG. 1, the proximal end 14 of the lead body 12 may include one or more connectors 48 (best seen in FIG. 3) to electrically couple the lead 10 to an implantable cardioverter-defibrillator (ICD) 50 subcutaneously implanted within the patient, for example, under the left armpit of the patient. The ICD 50 may include a housing 52 that forms a hermetic seal which protects the components of ICD 50. The housing 52 of ICD 50 may be formed of a conductive material, such as titanium or titanium alloy, which may function as a housing electrode for a particular therapy vector. The ICD 50 may also include a connector assembly that includes electrical feedthroughs through which electrical connections are made between the one or more connectors 48 of lead 10 and the electronic components included within the housing 38. The housing 52 may house one or more processors, memories, transmitters, receivers, sensors, sensing circuitry, therapy circuitry, power sources (capacitors and batteries) and/or other appropriate components. The ICD 50 may generate and deliver electrical stimulation therapy such as anti-tachycardia pacing, cardioversion or defibrillation shocks, post-shock pacing, bradycardia pacing, or other electrical stimulation Referring now to FIG. 5, in another configuration, a lead 54 is shown having a lead body 12 and the substantially the same features as discussed above with respect to the features of lead 10. However, lead 54 includes a third defibrillation electrode 56. The third defibrillation electrode 56 may have the same properties and construction as the first and second defibrillation electrodes 22 and 24 in that it may be mechanically coupled and/or electrically coupled within the tip 46. In one configuration, the proximal end of third defibrillation electrode 56 may be retained within the joint 36 and may expand and collapse in the same manner as the first and second defibrillation electrodes 22 and 24. In another configuration the third defibrillation electrode 56 may be fixed in the collapsed configuration by being mounted to the shaft 42 at the proximal and electrically coupled to the tip 46. In such a configuration, the third defibrillation electrode 56 may extend longitudinally along the major longitudinal axis of the shaft 42 and be disposed on the opposite side of the shaft 42 to which the plurality of electrodes 44 are disposed. Although three defibrillation electrodes are illustrated in FIG. 5, it is contemplated that any number of defibrillation electrodes may be coupled to the treatment portion 18 either to the same conductor as each defibrillation electrode or separate conductors.

In yet another embodiment, shaft 42 may not include any electrodes 44. Instead, electrodes 44 may be placed on along a segment that extends from tip 46 to joint 36 and that expands and collapses in the same manner as the first and second defibrillation electrodes 22 and 24 (similar to defibrillation electrode 56 of FIG. 5). In this case, the expandable/collapsible segment that includes electrodes 44 would expand in a direction that is not in the same plane as the defibrillation electrodes 22 and 24 and shaft 42. Instead, the expandable/collapsible segment including electrodes 44 would extend away from the lead body, e.g., at an oblique or right angle (perpendicular) relative to the plane defined by electrodes 22, 24, and shaft 42. In this manner, when expanded, the segment having electrodes 44 would extend toward the heart of the patient thus putting electrodes 44 in a position closer to the heart. This may provide lower pacing capture thresholds as well as better sensed cardiac electrical signals.

Figure 6:
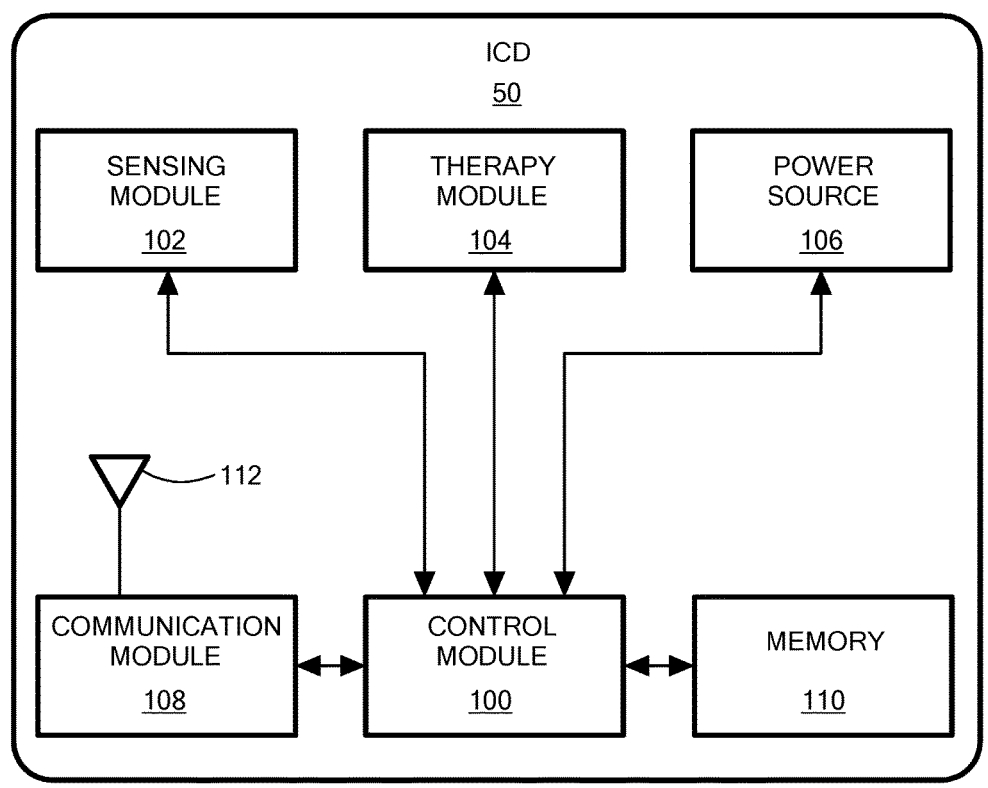
FIG. 6 is a functional block diagram of an example configuration of electronic components of an example ICD.

FIG. 6 is a functional block diagram of an example configuration of electronic components of an example ICD 50. ICD 50 includes a control module 100, sensing module 102, therapy module 104, communication module 108, and memory 110. The electronic components may receive power from a power source 106, which may be a rechargeable or non-rechargeable battery. In other embodiments, ICD 50 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components. FIG. 6 will be described in the context of ICD 50 being coupled to lead 10 for exemplary purposes only. However, ICD 50 may be coupled to other leads, such as lead 54 described herein, and thus other electrodes, e.g., electrode 56.

Sensing module 102 is electrically coupled to some or all of electrodes 22, 24, or 44 via the conductors of lead 10 and one or more electrical feedthroughs, or to the housing electrode via conductors internal to the housing of ICD 50. Sensing module 102 is configured to obtain signals sensed via one or more combinations of electrodes 22, 24, or 44 and/or the housing electrode of ICD 50 and process the obtained signals.

The components of sensing module 102 may be analog components, digital components or a combination thereof. Sensing module 102 may, for example, include one or more sense amplifiers, filters, rectifiers, threshold detectors, analog-to-digital converters (ADCs) or the like. Sensing module 102 may convert the sensed signals to digital form and provide the digital signals to control module 100 for processing or analysis. For example, sensing module 102 may amplify signals from the sensing electrodes and convert the amplified signals to multi-bit digital signals by an ADC. Sensing module 102 may also compare processed signals to a threshold to detect the existence of atrial or ventricular depolarizations (e.g., P- or R waves) and indicate the existence of the atrial depolarization (e.g., P-waves) or ventricular depolarizations (e.g., R-waves) to control module 100.

Control module 100 may process the signals from sensing module 102 to monitor electrical activity of the heart of the patient. Control module 100 may store signals obtained by sensing module 102 as well as any generated EGM waveforms, marker channel data or other data derived based on the sensed signals in memory 110. Control module 100 may analyze the EGM waveforms and/or marker channel data to detect cardiac events (e.g., tachycardia). In response to detecting the cardiac event, control module 100 may control therapy module 104 to deliver the desired therapy to treat the cardiac event, e.g., defibrillation shock, cardioversion shock, ATP, post-shock pacing, or bradycardia pacing.

Therapy module 104 is configured to generate and deliver electrical stimulation therapy to the heart. Therapy module 104 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy module 104 may include a first set of components configured to provide pacing therapy and a second set of components configured to provide defibrillation therapy. In other instances, therapy module 104 may utilize the same set of components to provide both pacing and defibrillation therapy. In still other instances, therapy module 104 may share some of the defibrillation and pacing therapy components while using other components solely for defibrillation or pacing.

Control module 100 may control therapy module 104 to deliver the generated therapy to the heart via one or more combinations of electrodes 22, 24, or 44 of lead 10 and the housing electrode of ICD 50 according to one or more therapy programs, which may be stored in memory 110. In instances in which ICD 50 is coupled to a different lead, e.g., lead 54, other electrodes may be utilized, such as electrode 56. Control module 100 controls therapy module 104 to generate electrical stimulation therapy with the amplitudes, pulse widths, timing, frequencies, electrode combinations or electrode configurations specified by a selected therapy program.

Therapy module 104 may include a switch module to select which of the available electrodes are used to deliver the therapy. The switch module may include a switch array, switch matrix, multiplexer, or any other type of switching device suitable to selectively couple electrodes to therapy module 104. Control module 100 may select the electrodes to function as therapy electrodes, or the therapy vector, via the switch module within therapy module 104. In instances in which defibrillation electrodes 22 and 24 are each coupled to separate conductors, control module 100 may be configured to selectively couple therapy module 104 to either one of defibrillation electrodes 22 and 24 individually or couple to both of the defibrillation electrodes 22 and 24 concurrently. In some instances, the same switch module may be used by both therapy module 104 and sensing module 102. In other instances, each of sensing module 102 and therapy module 104 may have separate switch modules.

In the case of pacing therapy being provided, e.g., ATP, post-shock pacing, and/or bradycardia pacing provided via electrodes 44 of lead 10, e.g., using an electrode vector in which one of electrodes 44 is functions at a first polarity and another one of electrodes 44 functions at a second polarity or one of electrodes 44 functions at a first polarity and the housing electrode functions at a second polarity. In some instances, defibrillation electrodes 22 and 24 may also be used to provide pacing. For example, therapy module 104 may deliver pacing (e.g., ATP or post-shock pacing) using an electrode vector that includes one or both defibrillation electrodes 22 and 24. The electrode vector used for pacing may be one of the defibrillation electrodes as an anode (or cathode) and the housing of ICD 50 as the cathode (or anode) or an electrode vector between the defibrillation electrodes 22 and 24 or between one of the defibrillation electrodes and one or more of electrodes 44. If necessary, therapy module 104 may generate and deliver a cardioversion/defibrillation shock (or shocks) using one or both of defibrillation electrodes 22 and 24 as a cathode and the housing electrode of ICD 50 as an anode.

Control module 100 controls therapy module 104 to generate and deliver pacing pulses with any of a number of shapes, amplitudes, pulse widths, or other characteristic to capture the heart. For example, the pacing pulses may be monophasic, biphasic, or multiphasic (e.g., more than two phases). The pacing thresholds of the heart when delivering pacing pulses from the substernal space may depend upon a number of factors, including location, type, size, orientation, and/or spacing of the electrodes, location of ICD 50 relative to the electrodes, physical abnormalities of the heart (e.g., pericardial adhesions or myocardial infarctions), or other factor(s).

The increased distance from the electrodes of lead 10 to the heart tissue may result in the heart having increased pacing thresholds compared to transvenous pacing thresholds. To this end, therapy module 104 may be configured to generate and deliver pacing pulses having larger amplitudes and/or pulse widths than conventionally required to obtain capture via leads implanted within the heart (e.g., transvenous leads) or leads attached directly to the heart. In one example, therapy module 104 may generate and deliver pacing pulses having amplitudes of less than or equal to 8 volts and pulse widths between 0.5-3.0 milliseconds and, in some instances up to 4 milliseconds. In another example, therapy module 104 may generate and deliver pacing pulses having amplitudes of between 5 and 10 volts and pulse widths between approximately 3.0 milliseconds and 10.0 milliseconds. In another example, therapy module 104 may generate and deliver pacing pulses having pulse widths between approximately 2.0 milliseconds and 8.0 milliseconds. In a further example, therapy module 104 may generate and deliver pacing pulses having pulse widths between approximately 0.5 milliseconds and 20.0 milliseconds. In another example, therapy module 104 may generate and deliver pacing pulses having pulse widths between approximately 1.5 milliseconds and 20.0 milliseconds.

Pacing pulses having longer pulse durations than conventional transvenous pacing pulses may result in lower energy consumption. As such, therapy module 104 may be configured to generate and deliver pacing pulses having pulse widths or durations of greater than two (2) milliseconds. In another example, therapy module 104 may be configured to generate and deliver pacing pulses having pulse widths or durations of between greater than two (2) milliseconds and less than or equal to three (3) milliseconds. In another example, therapy module 104 may be configured to generate and deliver pacing pulses having pulse widths or durations of greater than or equal to three (3) milliseconds. In another example, therapy module 104 may be configured to generate and deliver pacing pulses having pulse widths or durations of greater than or equal to four (4) milliseconds. In another example, therapy module 104 may be configured to generate and deliver pacing pulses having pulse widths or durations of greater than or equal to five (5) milliseconds. In another example, therapy module 104 may be configured to generate and deliver pacing pulses having pulse widths or durations of greater than or equal to ten (10) milliseconds. In a further example, therapy module 104 may be configured to generate and deliver pacing pulses having pulse widths between approximately 3-10 milliseconds. In a further example, therapy module 104 may be configured to generate and deliver pacing pulses having pulse widths between approximately 4-10 milliseconds. In a further example, therapy module 104 may be configured to generate and deliver pacing pulses having pulse widths or durations of greater than or equal to fifteen (15) milliseconds. In yet another example, therapy module 104 may be configured to generate and deliver pacing pulses having pulse widths or durations of greater than or equal to twenty (20) milliseconds.

Depending on the pulse widths, ICD 50 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 50 reduces the likelihood of extra-cardiac stimulation and lower consumed energy of power source 106.

For pacing therapy provided from the subcutaneous placement of lead 10 above the sternum and/or ribcage, pacing amplitudes and pulse widths may vary, e.g., be increased given the further distances from heart and the various anatomical features via which the energy must penetrate.

In the case of cardioversion or defibrillation therapy, e.g., cardioversion or defibrillation shocks provided by defibrillation electrodes 22 and 24 (individually or together), control module 100 controls therapy module 104 to generate cardioversion or defibrillation shocks having any of a number of waveform properties, including leading-edge voltage, tilt, delivered energy, pulse phases, and the like. Therapy module 104 may, for instance, generate monophasic, biphasic or multiphasic waveforms. Additionally, therapy module 104 may generate cardioversion or defibrillation waveforms having different amounts of energy. As with pacing, delivering cardioversion or defibrillation shocks from the substernal space, e.g., from defibrillation electrodes 22 and 24 substantially within anterior mediastinum 36, may reduce the amount of energy that needs to be delivered to defibrillate the heart. When lead 10 is implanted in the substernal space, therapy module 104 may generate and deliver cardioversion or defibrillation shocks having energies of less than 65 J, less than 100 J, between 40-50 J, between 35-100 J, and in some instances less than 35 J. When lead 10 is implanted subcutaneously, ICD 50 may generate and deliver cardioversion or defibrillation shocks having energies around 65-80 J.

Therapy module 104 may also generate defibrillation waveforms having different tilts. In the case of a biphasic defibrillation waveform, therapy module 104 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide substernal defibrillation via defibrillation electrodes 22 and 24.

Communication module 108 includes any suitable hardware, firmware, software or any combination thereof for communicating with another device, such as a clinician programmer, a patient monitoring device, or the like. For example, communication module 108 may include appropriate modulation, demodulation, frequency conversion, filtering, and amplifier components for transmission and reception of data with the aid of antenna 112. Antenna 112 may be located within connector block of ICD 50 or within housing ICD 50.

The various modules of ICD 50 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 110 may include computer-readable instructions that, when executed by control module 100 or other component of ICD 50, cause one or more components of ICD 50 to perform various functions attributed to those components in this disclosure. Memory 110 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The leads and systems described herein may be used at least partially within the substernal space, e.g., within anterior mediastinum of patient, to provide an extravascular ICD system. An implanter (e.g., physician) may implant the distal portion of the lead intra-thoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal end of lead 10 (or other lead described herein, e.g., leads 54) is introduced into tunnel via implant tool (e.g., via lumen or channel of the tool or a sheath). As described above, the defibrillation electrodes 22 and 24 push joint 36 toward a proximal end of lead 10 to transition defibrillation electrodes 22 and 25 from the expanded configuration 26 (seen in FIG. 3) to the collapsed configuration 40 (seen in FIG. 4). When disposed within the implant tool or sheath, the defibrillation electrodes 22 and 24 remain in the collapsed configuration 40. The defibrillation electrodes 22 and 24 may define a substantially linear configuration when in the collapsed configuration 40 such that the defibrillation electrodes 22 and 24 are substantially parallel with the major longitudinal axis of the lead body 12. Once the distal end of lead 10 is in place, the implant tool is withdrawn toward the incision and removed from the body of the patient while leaving lead 10 in place along the substernal path. As the implant tool is withdrawn, the defibrillation electrodes 22 and 24 transition from the collapsed configuration 40 to the expanded configuration 26.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

The invention claimed is:

1. An implantable medical electrical lead, comprising:
   an elongate lead body having a proximal end and a distal portion;
   a plurality of defibrillation electrodes coupled to the distal portion, the plurality of defibrillation electrodes being transitionable from a first configuration in which the defibrillation electrodes are biased in an expanded configuration to a second configuration in which the defibrillation electrodes are in a collapsed configuration; and
   a joint slideably disposed around a portion of the lead body, at least a portion of the plurality of defibrillation electrodes being coupled to the joint,
   wherein the joint is slideable between a first position in which the plurality of defibrillation electrodes are disposed in the first configuration to a second position in which the plurality of defibrillation electrodes are disposed in the second configuration, and wherein the first position of the joint is distal to the second position of the joint.

2. The lead of claim 1, wherein the elongate lead body defines a major longitudinal axis, and wherein when the plurality of electrodes are disposed in the second configuration, the plurality of electrodes are substantially parallel to the major longitudinal axis.

3. The lead of claim 1, wherein the plurality of defibrillation electrodes are symmetric with respect to each other when in the first configuration.

4. The lead of claim 1, wherein the joint is biased to be in the first position.

5. The lead of claim 1, wherein each of the plurality of defibrillation electrodes defines a proximal end and a distal end, and the implantable medical electrical lead further includes a shaft disposed between the proximal and distal ends of the plurality of defibrillation electrodes, the shaft including a plurality of electrodes.

6. The lead of claim 5, wherein the plurality of electrodes are configured to, at least one of, deliver pacing pluses to the heart and sense cardiac signals when the lead is implanted within a patient.

7. The lead of claim 5, wherein when the plurality of defibrillation electrodes are in the first configuration, the shaft and the plurality of defibrillation electrodes are substantially disposed in the same plane.

8. The lead of claim 5, wherein the shaft includes a first side and a second side opposite the first side, and wherein the plurality of electrodes are disposed on the first side.

9. The lead of claim 8, further comprising a third defibrillation electrode, wherein the third defibrillation electrode is disposed on the second side.

10. The lead of claim 5, wherein the implantable medical electrical lead further includes
    a segment that extends from the proximal and distal ends, the segment being transitionable from the first configuration in which the segment is biased in the expanded configuration to the second configuration in which the segment is in the collapsed configuration, wherein the segment includes one or more electrodes disposed along the segment.

11. The lead of claim 1, wherein when the plurality of defibrillation electrodes are in the first configuration, the plurality of defibrillation electrodes are substantially planar to each other.

12. The lead of claim 11, wherein when the plurality of defibrillation electrodes are in the first configuration, at least two of the plurality of defibrillation electrodes are substantially planar to each other and at least a third of the plurality of defibrillation electrodes extends substantially perpendicular to the at least two of the plurality of defibrillation electrodes being substantially planar to each other.

13. The lead of claim 11, further including a conductor in the lead body, and wherein the plurality of defibrillation electrodes are in electrical communication with the conductor.

14. The lead of claim 11, further including a plurality of conductors in the lead body, and wherein the plurality of defibrillation electrodes are in electrical communication with at least one of the conductors.

15. The lead of claim 1, wherein the plurality of defibrillation electrodes are configured to transition from the second configuration to the first configuration upon removal of a sheath.

16. The lead of claim 1, wherein at least one wall of a sheath pushes the plurality of defibrillation electrodes on the joint to collapse the plurality of defibrillation electrodes from the first configuration to the second configuration.

17. The lead of claim 1, wherein the plurality of defibrillation electrodes are fixedly connected to the joint.

18. An implantable medical electrical lead, comprising:
    an elongate lead body having a proximal end and a distal portion;

a plurality of defibrillation electrodes coupled to the distal portion, the plurality of defibrillation electrodes defining respective proximal and distal ends, the plurality of defibrillation electrodes being transitionable from a first configuration in which the defibrillation electrodes are biased in an expanded configuration in which the plurality of defibrillation electrodes extend radially outward from the lead body to a second configuration in which the defibrillation electrodes are in a collapsed configuration in which the plurality of defibrillation electrodes are substantially parallel to the lead body; and a joint slideably disposed around a portion of the lead body, the proximal ends of the plurality of the defibrillation electrodes being disposed within a portion of the joint, wherein the joint is slideable between a first position in which the plurality of defibrillation electrodes are disposed in the first configuration to a second position in which the plurality of defibrillation electrodes are disposed in the second configuration, and wherein the first position of the joint is distal to the second position of the joint.

19. The lead of claim 18, further including a conductor disposed within the lead body, and wherein the plurality of defibrillation electrodes are in electrical communication with the conductor.

20. The lead of claim 18, wherein when the plurality of defibrillation electrodes are in the first configuration, the plurality of defibrillation electrodes are substantially planar to each other.

21. The lead of claim 18, further including a plurality of electrodes disposed between the proximal and distal ends of the plurality of defibrillation electrodes.

22. The lead of claim 21, wherein the plurality of electrodes are coupled to a second conductor within the lead body, and wherein the plurality of electrodes are configured to have a different polarity compared to the polarity of the plurality of defibrillation electrodes.

23. The lead of claim 21, further including a shaft between the proximal and distal ends of the plurality of defibrillation electrodes, and wherein the plurality of electrodes are recessed within the shaft.

24. The lead of claim 23, wherein the shaft defines a major longitudinal axis, and wherein the plurality of electrodes are disposed along the major longitudinal axis of the shaft.

25. The lead of claim 18, wherein the plurality of defibrillation electrodes are configured to transition from the second configuration to the first configuration upon removal of a sheath.

26. The lead of claim 18, wherein the plurality of defibrillation electrodes are fixedly connected to the joint.

27. An implantable medical electrical lead, comprising:

an elongate lead body having a proximal end and a distal portion;

a plurality of defibrillation electrodes coupled to the distal portion, the plurality of defibrillation electrodes defining respective proximal and distal ends, the plurality of defibrillation electrodes being transitionable from a first configuration in which the defibrillation electrodes are biased in an expanded configuration in which the plurality of defibrillation electrodes extend radially outward from the lead body to a second configuration in which the defibrillation electrodes are in a collapsed configuration in which the plurality of defibrillation electrodes are substantially parallel to the lead body; and a joint slideably disposed around a portion of the lead body, the proximal ends of the plurality of the defibrillation electrodes being disposed within a portion of the joint, wherein the joint is slideable between a first position in which the plurality of defibrillation electrodes are disposed in the first configuration to a second position in which the plurality of defibrillation electrodes are disposed in the second configuration, and wherein the first position of the joint is distal to the second position of the joint;

a shaft disposed between the proximal and distal ends of the plurality of defibrillation electrodes, the shaft defining a first side and a second side opposite the first side, the shaft including a plurality of longitudinally spaced and recessed electrodes on the first side and at least one additional defibrillation electrode on the second side; and the joint abutting the proximal end of the shaft when the plurality of defibrillation electrodes are disposed in the first configuration.

* * * * *